US010013297B2

(12) United States Patent
Modzelewski et al.

(10) Patent No.: US 10,013,297 B2
(45) Date of Patent: Jul. 3, 2018

(54) ERROR DETECTION AND REJECTION FOR A DIAGNOSTIC TESTING SYSTEM

(71) Applicant: Trividia Health, Inc., Fort Lauderdale, FL (US)

(72) Inventors: Brent E. Modzelewski, Boca Raton, FL (US); Ferhan Kayihan, Tacoma, WA (US); Edward Cardello, Wellington, FL (US)

(73) Assignee: Trividia Health, Inc., Fort Lauderdale, FL (US)

( * ) Notice: Subject to any disclaimer, the term of this patent is extended or adjusted under 35 U.S.C. 154(b) by 416 days.

(21) Appl. No.: 14/683,484

(22) Filed: Apr. 10, 2015

(65) Prior Publication Data
US 2015/0212872 A1    Jul. 30, 2015

Related U.S. Application Data

(63) Continuation of application No. 11/734,473, filed on Apr. 12, 2007, now Pat. No. 9,029,157.

(51) Int. Cl.
*G01N 15/06* (2006.01)
*G01N 35/00* (2006.01)
(Continued)

(52) U.S. Cl.
CPC ... *G06F 11/0763* (2013.01); *G01N 33/48771* (2013.01); *G01N 35/00732* (2013.01); *G01N 2035/00851* (2013.01); *Y10T 436/11* (2015.01)

(58) Field of Classification Search
CPC .............................. G01N 35/00; G01N 15/06
USPC ........ 422/50, 68.1, 400, 420, 425, 430, 412, 422/67, 82.01, 82.05, 82.02, 502, 503; 436/43, 44, 48, 63, 68, 149, 164
See application file for complete search history.

(56) References Cited

U.S. PATENT DOCUMENTS 3,907,503 A   9/1975   Betts et al.
4,592,893 A   6/1986   Poppe et al.
(Continued)

FOREIGN PATENT DOCUMENTS

EP    0395384 A    10/1990
JP    H02-151763    6/1990
(Continued)

OTHER PUBLICATIONS

International Search report, PCT/US2008/059398, dated Jan. 13, 2009.
(Continued)

*Primary Examiner* — Brian J. Sines
(74) *Attorney, Agent, or Firm* — Greenberg Traurig, LLP; David J. Dykeman; Roman Fayerberg

(57) ABSTRACT

A system for measuring a property of a sample is provided. The system comprises a diagnostic measuring device having a memory and a diagnostic test strip for collecting the sample. The strip has embedded thereon a pattern representative of at least first data and second data, the first data being data representing at least one of parameters related to measuring the property, codes usable for calibration of the diagnostic measuring device, or parameters indicating proper connection between the measuring device and the test strip and the second data usable for detecting and rejecting potential errors affecting the proper measurement of the property.

4 Claims, 9 Drawing Sheets

(51) Int. Cl.
*G06F 11/07* (2006.01)
*G01N 33/487* (2006.01)

(56) References Cited

U.S. PATENT DOCUMENTS

| | | | |
|---|---|---|---|
| 4,787,398 A | | 11/1988 | Garcia et al. |
| 4,975,647 A | | 12/1990 | Downer et al. |
| 5,126,952 A | | 6/1992 | Kildal-Brandt et al. |
| 5,281,395 A | | 1/1994 | Markart et al. |
| 5,379,214 A | | 1/1995 | Arbuckle et al. |
| 5,408,535 A | | 4/1995 | Howard, III et al. |
| 5,439,826 A | | 8/1995 | Kontorovich |
| 5,873,990 A | | 2/1999 | Wojciechowski et al. |
| 5,945,341 A | | 8/1999 | Howard, III |
| 6,168,957 B1 | | 1/2001 | Matzinger et al. |
| 6,295,506 B1 | | 9/2001 | Heinonen et al. |
| 6,743,635 B2 | | 6/2004 | Neel et al. |
| 6,770,487 B2 | | 8/2004 | Crosby |
| 6,814,844 B2 | | 11/2004 | Bhullar et al. |
| 9,029,157 B2 | | 5/2015 | Modzelewski et al. |
| 2003/0111357 A1 | * | 6/2003 | Black .............. G01N 33/48757 205/775 |
| 2003/0124738 A1 | * | 7/2003 | Crosby .............. G01N 33/558 436/514 |
| 2004/0200721 A1 | * | 10/2004 | Bhullar .............. G01N 33/48771 204/403.01 |
| 2005/0019953 A1 | * | 1/2005 | Groll .............. G01N 33/48771 436/514 |
| 2005/0168747 A1 | * | 8/2005 | Fox .............. B01L 3/5023 356/446 |
| 2006/0094986 A1 | * | 5/2006 | Neel .............. A61B 5/14532 600/583 |
| 2006/0105359 A1 | | 5/2006 | Favuzzi et al. |
| 2007/0015286 A1 | * | 1/2007 | Neel .............. G01N 33/48771 436/149 |
| 2007/0110615 A1 | * | 5/2007 | Neel .............. G01N 33/48771 422/400 |
| 2007/0212258 A1 | * | 9/2007 | Neel .............. G01N 33/48757 422/400 |
| 2007/0233395 A1 | * | 10/2007 | Neel .............. A61B 5/0002 702/19 |
| 2011/0125530 A1 | * | 5/2011 | Drucker .............. A61B 5/743 705/3 |
| 2013/0332874 A1 | * | 12/2013 | Rosinko .............. G06F 3/0484 715/771 |

FOREIGN PATENT DOCUMENTS

| | | |
|---|---|---|
| JP | H03-011481 | 1/1991 |
| JP | H08-055180 | 2/1996 |
| JP | H10-332626 | 12/1998 |
| JP | 2000-019147 A | 1/2000 |
| JP | 2000-098037 A | 4/2000 |
| JP | 2003-156469 | 5/2003 |
| JP | 2004-243118 A | 9/2004 |
| JP | 2006-511788 | 4/2006 |
| JP | 2007-033459 A | 2/2007 |
| JP | 2009-501341 A | 1/2009 |
| TW | 559660 | 11/2003 |
| TW | 200608015 A | 3/2006 |
| TW | I265677 | 11/2006 |
| WO | 2004/113914 | 12/2004 |
| WO | 2004/113915 | 12/2004 |
| WO | 2006/103083 A1 | 10/2006 |
| WO | 2007/011569 A2 | 1/2007 |
| WO | 2007/011569 A3 | 1/2007 |

OTHER PUBLICATIONS

European Search Report, EP 10150368.8-2204, dated Mar. 1, 2010.
European Search Report, EP 10150369.6-2204, dated Mar. 4, 2010.
Examination Report issued in Australian Patent Application No. 2008239414 dated Sep. 18, 2012.
Office Action issued in Japanese Patent Application No. 2010-503134 dated Jun. 19, 2012.
Office Action issued in European Patent Application No. 10 150 369.6 dated Jul. 25, 2013.
Search Report issued in Taiwanese Patent Application No. 97111362 dated Nov 8, 2013.
PCT Written Opinion of the International Searching Authority issued in International Application No. OCT/US2008/059398 dated Oct. 12, 2009.
PCT International Preliminary Report on Patentability issued in International Application PCT/US2008/059398 dated Oct. 13, 2009.
Office Action issued in U.S. Appl. No. 11/734,473 dated Jan. 3, 2011.
Office Action issued in U.S. Appl. No. 11/734,473 dated Nov. 1, 2013.
Office Action issued in U.S. Appl. No. 11/734,473 dated Jun. 28, 2010.
Office Action issued in U.S. Appl. No. 11/734,473 dated Mar. 13, 2014.

* cited by examiner

Table 2

FIG. 12

ERROR DETECTION AND REJECTION FOR A DIAGNOSTIC TESTING SYSTEM

RELATED APPLICATIONS

This application is a continuation application of U.S. patent application Ser. No. 11/734,473, filed on Apr. 12, 2007, which application is incorporated herein by reference in its entirety.

FIELD

The present invention relates to error detection and rejection in systems and methods which electrochemically sense a particular constituent within a fluid through the use of diagnostic test strips.

BACKGROUND

Many industries have a commercial need to monitor the concentration of particular constituents in a fluid. In the health care field, individuals with diabetes, for example, have a need to monitor a particular constituent within their bodily fluids. A number of systems are available that allow people to test a body fluid, such as, blood, urine, or saliva, to conveniently monitor the level of a particular fluid constituent, such as, for example, cholesterol, proteins, and glucose. Individuals with diabetes, a pancreatic disorder characterized by insufficient insulin production, prevents the proper digestion of glucose, have a need to carefully monitor their blood glucose levels on a daily basis. A number of systems that allow people to conveniently monitor their blood glucose levels are available. Such systems typically include a test strip where the user applies a blood sample and a meter that "reads" the test strip to determine the glucose level in the blood sample.

Among the various technologies available for measuring blood glucose levels, electrochemical technologies are particularly desirable because only a very small blood sample may be needed to perform the measurement. In amperometric electrochemical-based systems, the test strip typically includes a sample chamber that contains reagents, such as glucose oxidase and a mediator, and electrodes. When the user applies a blood sample to the sample chamber, the reagents react with the glucose, and the meter applies a voltage to the electrodes to cause a redox reaction. The meter measures the resulting current and calculates the glucose level based on the current. Other systems based on coulometry or voltametry are also known.

Because the test strip includes a biological reagent, every strip manufactured is not reproducible with the exact same sensitivity. Therefore, test strips are manufactured in distinct lots and data particular to that lot is often used as a signal by the meter's microprocessor to assist in accurately performing the meter calculation. The data is used to help accurately correlate the measured current with the actual glucose concentration. For example, the data could represent a numeric code that "signals" the meter's microprocessor to access and utilize a specific set of stored calibration values from an on-board memory device during calculation.

In past systems, the code particular to a specific lot of strips has been input into the meter manually by the user, or connected through some type of memory device (such as a ROM chip) packaged along with test strips from a single manufacturing lot. This step of manual input, or connection by the user, adds to the risk of improperly inputting the wrong code data. Such errors can lead to inaccurate measurements and an improper recording of the patient's history. Past systems have also included bar-code readable information incorporated onto individual strips. Individually imprinting a particular bar-code on each strip adds significant manufacturing costs to the strip production and requires the additional expense of a bar-code reader incorporated within the meter in order to obtain the information.

It should be emphasized that accurate measurements of concentration levels in a body fluid, such as blood, may be critical to the long-term health of many users. As a result, there is a need for a high level of reliability in the meters and test strips used to measure concentration levels in fluids. Thus, it is desirable to have a cost effective auto-calibration system for diagnostic test strips that more reliably and more accurately provides a signaling code for individual test strips.

Embedding strip lot calibration information onto individual test strips which is readable by the instrument (meter), eliminates the need for the user to match the meter's lot calibration to the vial of strips. No longer needing to rely on the user to properly calibrate the meter's lot code removes the possibility of user error for this critical step.

Although user technique error is eliminated from automatically calibrated systems, the system is still subject to potential instrument read errors due to normal variations in production of strips and instruments. These systems are susceptible to erroneously read calibration codes whether the lot code is embedded electrically, mechanically, optically or otherwise. Abating or at least reducing the chance for a instrument read error will greatly enhance the reliability of the system.

Complete elimination of read error is possible, but is limited by the number of useful data bits that can be encoded on the small strip structure. Minimizing read errors is possible without sacrificing the number of available data bits for auto-calibration, but requires proper mathematical arrangement of and numbering of lot codes. A combination of the techniques taught in the invention described below can be employed to vary the read error rejection up to 100%, depending on a predetermined acceptable level of error rejection.

On-strip coding is a relatively new concept in glucose testing, which has the potential to greatly improve the accuracy of glucose readings. Systems that do not protect against test strip coding errors, either through detecting and rejecting strips which contain errors, or correcting read errors, will be subject to suboptimal performance and may produce inaccurate glucose readings.

SUMMARY

Embodiments of the present invention are directed to a system for measuring a property of a sample, a method for determining a constituent level within a fluid, and a method for encoding a code comprising a plurality of bits on a diagnostic test strip for determining a constituent level within a fluid comprising, such that impacts of possible bit errors are minimized that obviate one or more of the limitations and disadvantages of prior devices and methods.

One embodiment consistent with the present invention is directed to a system for measuring a property of a sample, comprising a diagnostic test strip for collecting the sample, the strip having information embedded thereon; a diagnostic measuring device for receiving the test strip, reading the embedded information, and measuring the sample; and the diagnostic device further comprising an error detection routine for detecting errors reading the embedded information.

Another embodiment consistent with the present invention is directed to a system for measuring a property of a sample, comprising a diagnostic measuring device having a memory; a diagnostic test strip for collecting the sample, the strip having a conductive pattern embedded thereon, the conductive pattern being representative of at least first data and second data, wherein the first data being data representing at least one of parameters related to measuring the property, codes usable for calibration of the diagnostic measuring device, or parameters indicating proper connection between the measuring device and the test strip; and the second data usable for detecting and rejecting potential errors affecting the proper measurement of the property.

Another embodiment consistent with the present invention is directed to a method of determining a constituent level within a fluid comprising providing a diagnostic test meter, the test meter comprising a memory and a processor; providing a diagnostic test strip, the test strip comprising at least one code embedded thereon; inserting the test strip into the test meter, the test meter reading the at least one code; performing an error detection and rejection algorithm on the at least one code; and determining the constituent level of the fluid if the error detection and rejection algorithm does not detect an error.

Another embodiment consistent with the present invention provides a method for minimizing the impact of potential errors that may occur when a device reads a diagnostic test strip including a first code comprising a plurality of bits arranged in a physical arrangement, the comprising: determining a probability of each bit to cause a read error, constructing a logical arrangement of the bits different than the physical arrangement based on the probability, wherein the logical arrangement comprises the bits arranged such that the impact of potential read errors is minimized.

Additional features and advantages of the invention will be set forth in part in the description which follows, and in part will be obvious from the description, or may be learned by practice of the invention. The features and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

FIG. 12 provides Table 2, which shows the results of Table 1 using an error grid.

DETAILED DESCRIPTION

Figure 1:
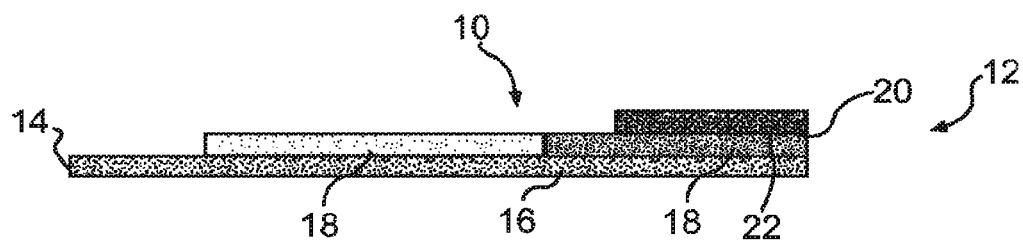
FIG. 1 is a general cross-sectional view of a test strip according to an embodiment of the present invention.

Reference will now be made in detail to the present embodiments of the invention, examples of which are illustrated in the accompanying drawings. Wherever possible, the same reference numbers will be used throughout the drawings to refer to the same or like parts.

According to exemplary embodiments, the invention relates to a system for measuring a body fluid constituent which includes a test strip and a meter, and detecting, rejecting, and minimizing any errors that may occur. An individual test strip may also include an embedded code relating to data associated with test strips belonging to a particular lot, data particular to that individual strip, and preferably data associated with detecting, rejecting and minimizing errors. The embedded information presents data readable by the meter signaling the meter's microprocessor to access and utilize a specific set of calibration parameters stored in a memory particular to test strips from a manufacturing lot to which the individual strip belongs, or to an individual test strip. The embedded information further includes data readable by the meter relating to detecting, rejecting, or correcting any errors. For purposes of this disclosure, "distal" refers to the portion of a test strip further from the device operator during normal use and "proximal" refers to the portion closer to the device operator during normal use.

The test strip may include a sample chamber for receiving a user's fluid sample, such as, for example, a blood sample. The sample chamber and test strip of the present specification can be formed using materials and methods described in commonly owned U.S. Pat. No. 6,743,635, which is hereby incorporated by reference in its entirety. Accordingly, the sample chamber may include a first opening in the proximal end of the test strip and a second opening for venting the sample chamber. The sample chamber may be dimensioned so as to be able to draw the blood sample in through the first opening, and to hold the blood sample in the sample chamber, by capillary action. The test strip can include a tapered section that is narrowest at the proximal end, or can include other indicia in order to make it easier for the user to locate the first opening and apply the blood sample. The meter and test strip may be such as described in U.S. patent application Ser. No. 11/181,778, which is hereby incorporated by reference in its entirety, and described below.

A working electrode and counter electrode can be disposed in the sample chamber optionally along with fill-detect electrodes. A reagent layer is disposed in the sample chamber and preferably contacts at least the working electrode. The reagent layer may include an enzyme, such as glucose oxidase, and a mediator, such as potassium ferricyanide or ruthenium hexamine. The test strip has, near its distal end, a first plurality of electrical strip contacts that are electrically connected to the electrodes via conductive traces. In addition, the test strip may also include a second plurality of electrical strip contacts near the distal end of the strip. The second plurality of electrical contacts can be arranged such that they provide, when the strip is inserted into the meter, a distinctly discernable lot code readable by the meter. As noted above, the readable code can be read as a signal to access data, such as calibration coefficients, from an on-board memory unit in the meter related to test strips from that lot, or even information corresponding to individual test strips, and preferably information relating to detecting, rejecting, or correcting possible errors.

The meter may be battery powered and may stay in a low-power sleep mode when not in use in order to save power. When the test strip is inserted into the meter, the first and second plurality of electrical contacts on the test strip contact corresponding electrical contacts in the meter. The second plurality of electrical contacts may bridge a pair of electrical contacts in the meter, causing a current to flow through a portion of a second plurality of electrical contacts. The current flow through the second plurality of electrical contacts causes the meter to wake up and enter an active mode. The meter also reads the code information provided by the second plurality of electrical contacts and can then identify, for example, the particular test to be performed, or a confirmation of proper operating status or the type of error detection, rejection, or correction method, algorithm, or routine being applied. In addition, the meter can also identify the inserted strip as either a test strip or a check strip based on the particular code information. If the meter detects a check strip, it performs a check strip sequence. If the meter detects a test strip, it performs a test strip sequence. Moreover, the meter can perform a error detection, error rejection, or error correction routine based on the code information. Consistent with an embodiment of the present invention the meter may have an internal memory therein, which can store microprocessor algorithms for performing calibrations, or an error detection, rejection, or correction method, routine, or algorithm. The internal memory within the meter may also store a firmware, which contains instructions for performing a stored microprocessor algorithm, an error detection, rejection, or correction method, routine, or algorithm, and instructions for the general operation of the meter. Moreover, consistent with an embodiment of the present invention, the firmware may be upgradeable, allowing for additional or alternative instructions to be stored in the internal memory.

In the test strip sequence, the meter validates the working electrode, counter electrode, and, if included, the fill-detect electrodes, by confirming that there are no low-impedance paths between any of these electrodes. If the electrodes are valid, the meter indicates to the user that sample may be applied to the test strip. The meter then applies a drop-detect voltage between the working and counter electrodes and detects a fluid sample, for example, a blood sample, by detecting a current flow between the working and counter electrodes (i.e., a current flow through the blood sample as it bridges the working and counter electrodes). To detect that an adequate sample is present in the sample chamber and that the blood sample has traversed the reagent layer and mixed with the chemical constituents in the reagent layer, the meter may apply a fill-detect voltage between the fill-detect electrodes and measures any resulting current flowing between the fill-detect electrodes. If this resulting current reaches a sufficient level within a predetermined period of time, the meter indicates to the user that adequate sample is present and has mixed with the reagent layer.

FIG. 1 illustrates a general cross-sectional view of an embodiment of a test strip 10 consistent with the present invention. Test strip 10 may comprise a test strip as described in U.S. patent application Ser. No. 11/181,778, incorporated herein by reference in its entirety. Test strip 10 includes a proximal connecting end 12, a distal end 14, and is formed with a base layer 16 extending along the entire length of test strip 10. Base layer 16 is preferably composed of an electrically insulating material and has a thickness sufficient to provide structural support to test strip 10. Disposed on base layer 16 is a conductive pattern (not shown).

The conductive pattern (not shown) includes a plurality of electrodes disposed on base layer 16 near proximal end 12, a plurality of electrical strip contacts disposed on base layer 16 near distal end 14, and a plurality of conductive traces electrically connecting the electrodes to the plurality of electrical strip contacts, the contacts being an area intended for mechanical engagement with another corresponding contact. In an embodiment consistent with the present invention, the plurality of electrodes may include a working electrode, a counter electrode, and fill-detect electrodes.

A dielectric insulating layer 18 may be formed over the conductive pattern along a portion of the test strip between the measuring electrodes and the plurality of electrical strip contacts in order to prevent scratching, and other damage, to the electrical connection. As seen in FIG. 1, the proximal end 12 of test strip 10 includes a sample receiving location, such as a sample chamber 20 configured to receive a user's fluid sample. The sample chamber 20 may be formed in part through a slot formed between a cover 22 and the underlying measuring electrodes formed on base layer 16. The relative position of the measuring electrodes and the electrical strip contacts form a proximal electrode region 24 at one end of strip 10 and a distal strip contact region 26 at the other end.

Figure 2:
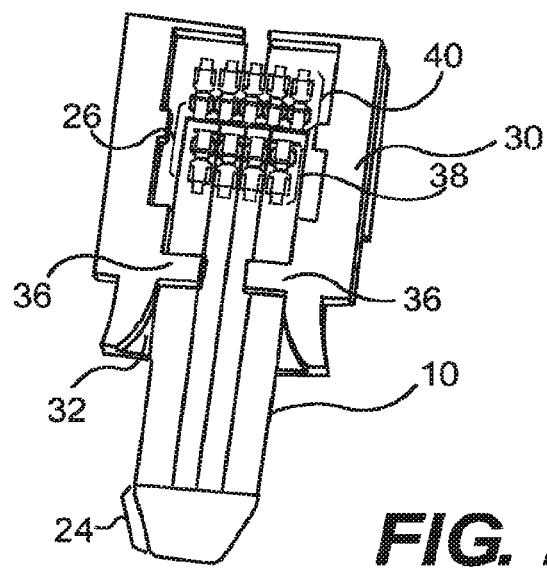
FIG. 2 is a top perspective view of a test strip inserted within a meter strip connector according to an embodiment of the present invention.

FIG. 2 illustrates a top perspective view of a test strip 10 inserted within a meter connector 30 consistent with the present invention. Test strip 10 includes a proximal electrode region 24, which contains the sample chamber and measuring electrodes, as described above. Proximal electrode region 24 may be formed to have a particular shape in order to distinguish to the user the end receiving a fluid sample from distal strip contact region 26. Meter connector 30 includes channel 32 extending out to a flared opening for receiving the test strip 10. Meter connector 30 may further include tangs 36 extending a predetermined height above the base of channel 32. The predetermined height of tangs 36 is selected to limit the extent, such as through a corresponding raised layer of test strip 10, to which a test strip 10 can be inserted into channel 32.

Meter connector 30 further includes a first plurality of connector contacts 38, disposed closer to the proximal end of meter connector 30, and a second plurality of connector contacts 40 disposed closer to the distal end of meter connector 30.

Figure 3:
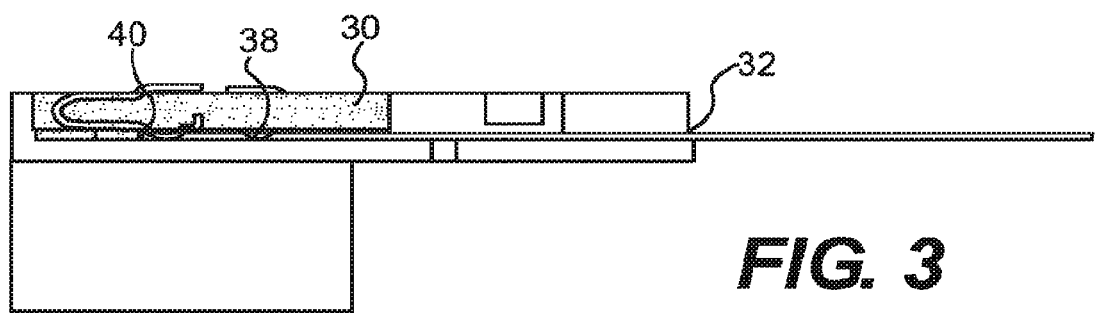
FIG. 3 is a general cross-sectional view of a test strip inserted within a meter strip connector according to an embodiment of the present invention.

FIG. 3 illustrates a general cross-sectional view of a test strip inserted within meter connector 30 consistent with the present invention. Channel 32 depicts a proximal row of connectors comprising a first plurality of connector contacts 38. In addition, channel 32 houses a distal row of connectors comprising a second plurality of connector contacts 40. First plurality of connector contacts 38 and second plurality of connector contacts 40 make contact with distinct portions of distal strip contact region 26.

Connector contacts may have either levels of high or low impedance, producing a code yielding a code index. In an embodiment consistent with the present invention, the code is a binary code based on the number of contact pads (P) implemented, where the number (N) of codes is equal to $N=2^P$. Although an embodiment consistent with the present invention utilizes a binary code, other types of codes may be used consistent with the present invention, and embodiments are not limited thereto.

However, another embodiment consistent with the present invention incorporates an auto-on/wake-up feature, and the number of codes possible when integrated with an auto-on/wake-up feature, however, is reduced to $N=2^P-1$. In a system having an auto-on/wake-up feature, a code with all zeros (all high impedance) is not an active code as it will not wake up the meter. The code, whether the possible number is $2^P$ or $2^P-1$, includes encoded test information, calibration information, and information relating to error detection, rejection, minimization or correction. Because the number of possible codes is limited by the number of contact pads, it is important to use a method of error detection, rejection, or correction which does not exhaust the possible code space, and allows sufficient test and calibration information to be encoded on test strip 10.

When test strip 10 is inserted into meter connector 30, one contact is closed and wakes up the meter by pulling the microcontroller's interrupt either high or low. The meter will then check the voltage out ($V_{out}$) to determine the test type and then read the code bits to determine the code value. The code value selected can, for example, be associated with a stored set of coefficients in the meter's memory for use in a glucose mapping algorithm that is particularly correlated to the reagent applied to the measuring electrode region. This code can also be associated with other types of strip parameter information, such as those referenced above. It could also select different meter configuration options as well. This can also be used to determine strip identification (check strip, manufacturing probe, and different test type). Furthermore, the code can be indicative of an error detection, rejection, correction routine, method, or algorithm.

The incorporation of individualized code data within individual test strips provides numerous advantages in addition to those associated with accuracy of measurement. For example, with individual strip coding a user no longer needs to manually enter the meter's lot code, eliminating the possibility of user technique error for this critical step. Strip lot codes stored directly on individual test strips will also provide a means to ship mixed lots of strips in a single strip vial. In contrast, current technologies such as button/key coding require all strips (typically packaged in a vial including 50 strips from the same lot) in a vial to be from the same lot code.

Figure 4:
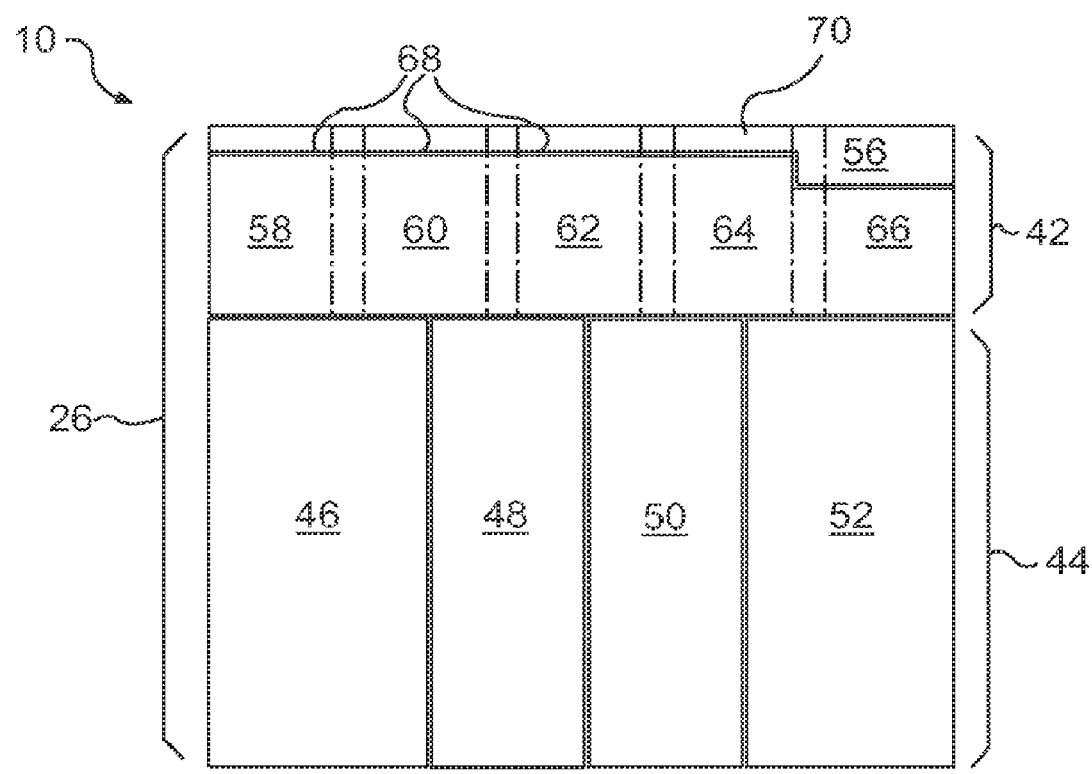
FIG. 4 is a top view of a distal portion of a test strip illustrating a distal strip contact region, consistent with an embodiment of the present invention.

FIG. 4 is a top view of a distal portion of test strip 10 illustrating distal strip contact region 26, consistent with an embodiment of the present invention. The conductive pattern (not shown) formed on base layer 16 extends along test strip 10 to include distal strip contact region 26. Distal strip contact region 26 is divided to form distinct conductive regions 42 and 44. Conductive region 44 is divided into four columns forming a first plurality of electrical strip contacts, labeled 46, 48, 50, and 52 respectively. First plurality of electrical strip contacts 46, 48, 50, and 52 are electrically connected to the plurality of measuring electrodes at the distal end of the test strip 10. It should be understood that the number of the first plurality of electrical strip contacts 46, 48, 50, and 52 are merely exemplary, and the system could include fewer or more electrical strip contacts corresponding to the number of measuring electrodes included in the system.

First plurality of electrical strip contacts 46, 48, 50, and 52 are divided, for example, through breaks 54 formed through the underlying conductive pattern (not shown) in test strip 10. An additional break 54 divides conductive region 44 from conductive region 42 within distal strip contact region 26, and a further break 54 separates the upper right-hand portion of distal strip contact region 26 to form a notch region 56, as will be described more fully in detail below.

Conductive region 42 is divided into five distinct regions outlining a second plurality of electrical strip contacts forming contacting pads 58, 60, 62, 64, and 66. As noted above, the conductive pattern on base layer 16 can be applied to the top side of the strip, the bottom side of the strip, or a combination of both. Contacting pads 58, 60, 62, 64, and 66 are configured to be operatively connected to the second plurality of connector contacts 40 within meter connector 30. Through this operative connection, the meter is presented with, and reads from the contacting pads, a particular code representing information signaling the meter to access data related to test strip 10. The breaks 68 isolate an outermost distal connecting end 70 of the distal strip contact region 26.

Figure 5:
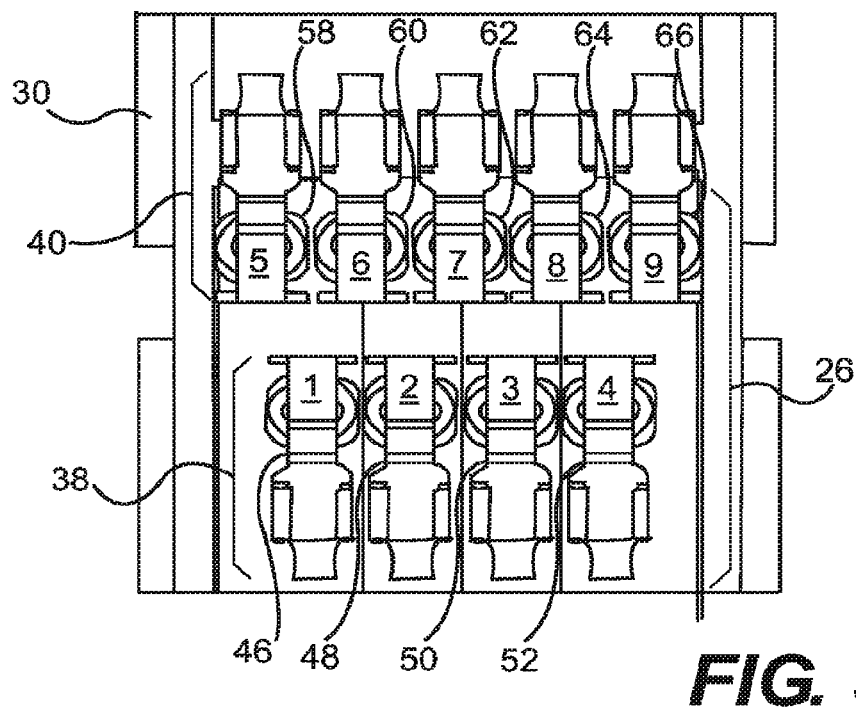
FIG. 5 illustrates a meter strip connector receiving a distal strip contact region of test strip consistent with the present invention.

FIG. 5 illustrates meter connector 30 receiving distal strip contact region 26 of test strip 10 consistent with the present invention. FIG. 5 depicts first plurality of connector contacts 38, labeled 1-4 respectively, and second plurality of connector contacts 40, labeled 5-9 Connector contacts 38 and 40 make contact with distinct portions of distal strip contact region 26. In particular, upon proper insertion of test strip 10 into connector 30, first plurality of electrical strip contacts 46, 48, 50, and 52 are respectively electrically connected to connector contacts 1-4, which form first plurality of connector contacts 38. Similarly, contacting pads 58, 60, 62, 64, and 66, which form the second plurality of electrical strip contacts, are respectively electrically connected to connector contacts 5-9, which form second plurality of connector contacts 40.

In an embodiment consistent with the present invention, the connection between contacting pad 66 and connector contact 9 establishes a common connection to ground (or a voltage source where the polarity is reversed), thereby completing an electric circuit, which includes the meter and at least a portion of conductive region 42. The completion of this circuit can perform a meter wake-up function, providing a signal to the meter to power up from low-power sleep mode. Accordingly, connector contact 9 may be positioned proximally relative to the remaining contacts 5-8, in order to ensure that contacts 5-8 are in proper connecting position prior to the final closing/wake-up of the circuit through the connection of contacting pad 66 and connector contact 9. Furthermore, because in another embodiment consistent with the present invention, a non-conductive insulating ink strip can be formed at the distal end of the test strip 10 and also because a conducting substance can be removed from notch region 56 (shown in FIG. 4), premature wake-up of the meter may be prevented.

That is, distal movement of test strip 10 within the connector channel 32 does not establish a common connection at the point connector contact 9 engages the extreme distal edge of test strip 10. Rather, a common connection will be established only when the connector contact passes notch 56, and ink strip if applied, and engages a conductive portion of contacting pad 66, providing a reliable connection.

As noted above, contacting pads 58, 60, 62, 64, and 66 are configured to be operatively connected to second plurality of connector contacts 40 within meter connector 30. Through this operative connection, the meter is presented with, and reads from the contacting pads, a particular code signaling the meter to access information related to test strip 10. The coded information may signal the meter to access data including, but not limited to, parameters indicating the particular test to be performed, parameters indicating connection to a test probe, parameters indicating connection to a check strip, calibration coefficients, temperature correction coefficients, ph level correction coefficients, hematocrit correction data, and data for recognizing a particular test strip brand. In addition, the coded information may be indicative of a error detection, rejection, or correction method.

Figure 6:
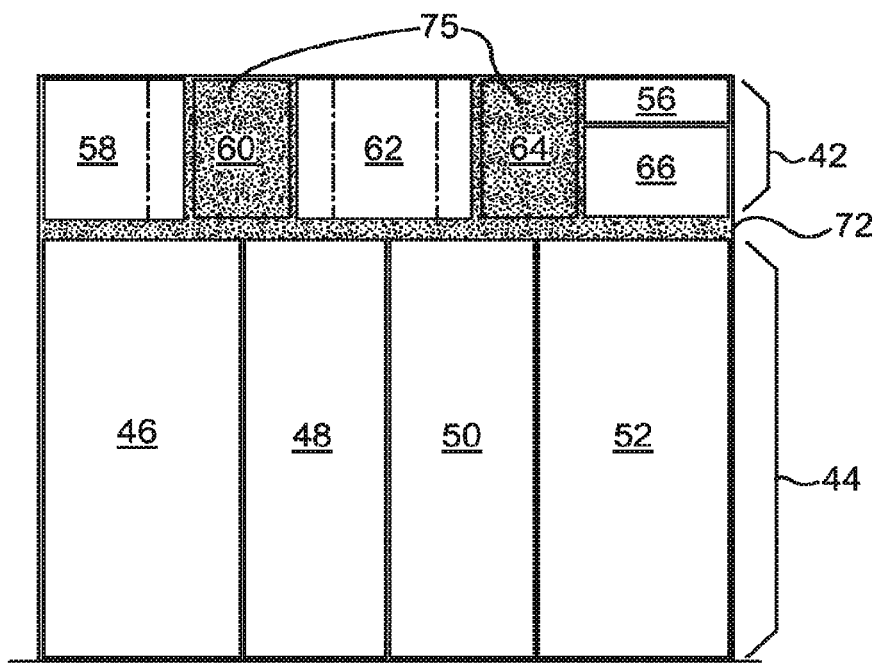
FIG. 6 illustrates an test strip having a sample code embedded thereon, consistent with the present invention.

FIG. 6 illustrates an test strip having a sample code embedded thereon, consistent with the present invention. As shown in FIG. 6, conductive contacting pads 60 and 64 are overprinted with an electrical insulating material, such as, for example, a non-conductive (insulating) ink layer 75. Non-conductive ink layer 75 increases the impedance between the corresponding connector contacts (in this example, connector contacts 6 and 8) and the underlying strip portion at various predetermined contacting pads within the conductive region 42 of distal strip contact region 26.

Upon connection of contacting pads 58, 60, 62, 64, and 66 to corresponding connector contacts 40, the meter will read a particular code based on the number, and pattern, of contacting pads overprinted with non-conductive ink layer 75. That is, the use of non-conductive ink layer 75, provides a switching network to be read by the meter. When an insulator is printed over one of the conductive surfaces of contacting pads 58, 60, 62, 64, and 66, it prevents the flow of electric current therealong and alters the conductive path between the contacting pad and connector contact. When no insulator is printed over the conductor current flow is relatively unimpeded.

Upon reading a particular code, an internal memory within the meter can access, through a stored microprocessor algorithm, specific calibration information relating to the particular test strip, or an error detection, rejection, or correction method, routine, or algorithm. The meter can read the code through either an analog or digital method. In the analog mode, a preset resistive ladder is interconnected within the meter to the second plurality of connector contacts 40 (labeled 5-9 in FIG. 5) such that permutations of printed non-conductive ink can be correlated to a distinct lot code using a voltage drop, resistance, or current measurement. The analog method also can be simultaneously used as the auto-on/wake-up feature as long as each code has at least one pad free of non-conductive ink that can make a low impedance connection to wake the meter up by closing an open circuit. The analog voltage, resistance, or current level could be used to signal the meter to access any of the data referenced above particular to test strip 10.

Figure 7:
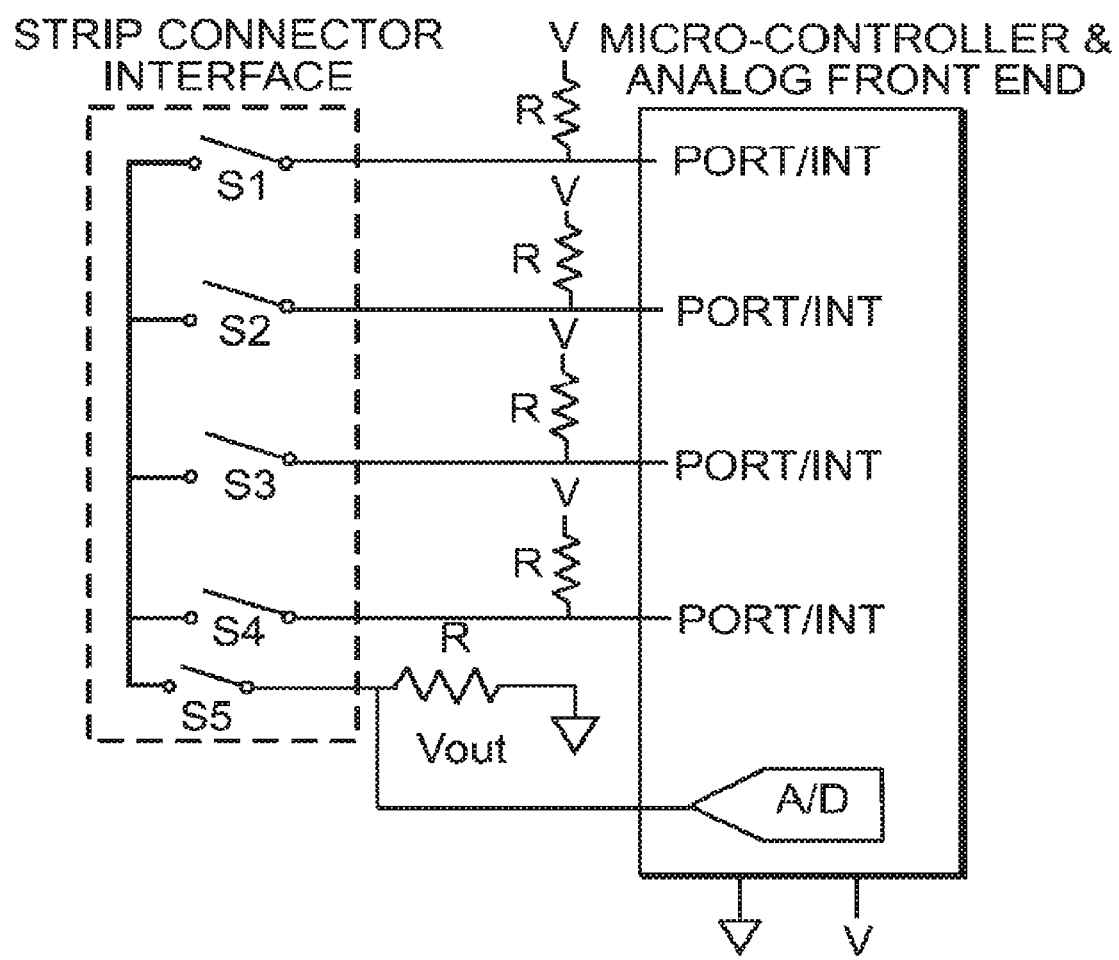
FIG. 7 is a schematic circuit representation of the meter strip connector and the meter micro-controller operating in a digital mode, consistent with the present invention.

In a digital mode, as schematically represented in FIG. 7, each contacting pad 58-66, would be read as an individual input, unlike the single input used by the analog method. For the digital method to be simultaneously used as an auto-on/ wake-up feature, the inputs would need to be wire-orred together or connected to an interrupt controller of a microcontroller. Each code must have at least one pad free of non-conductive ink 75 such that a low impedance connection can be made to wake-up the meter's micro-controller.

Non-conductive ink 75 with levels of high and low impedance produce a binary code yielding a code index based on the number of pads (P) implemented, where the number of codes is $N=2^P$. It is possible, however, for a code to comprise an arrangement where none of the electrical strip contacts are covered with electrical insulating material (a code will all logical "1"s, i.e. all conductors). As discussed above, the number of codes possible when integrated with an auto-on/wake-up feature, however, is reduced to $N=2^P-1$. In a system having an auto-on/wake-up feature, a code with all zeros (all insulators) is not an active code as it will not wake up the meter.

When test strip 10 is inserted into meter connector 30, one contact is closed and wakes up the meter by pulling the microcontroller's interrupt either high or low. The meter will then check the voltage out (Vout) to determine the test type and then read the code bits (S1, S2, S3, S4) to determine the code value. The code value selected can, for example, be associated with a stored set of coefficients in the meter's memory for use in a glucose mapping algorithm that is particularly correlated to the reagent applied to the measuring electrode region. In addition, the code value selected can be associated with an error detection, rejection, or correction algorithm. The voltage drop across the series resistor R at Vout in FIG. 7 can be sensed, to determine if code vales are within a predetermined range for use as a confirmation signal. This can also be used to determine strip identification (check strip, manufacturing probe, and different test type).

In addition to providing either a high or low impedance level (through the application or absence of an insulating layer of non-conductive ink 75 over one of the contacting pads) a particular resistive element may be applied over a particular contacting pad. The resistive element introduces an increased level of impedance into a circuit that reduces (but does not necessarily prevent) the flow of electric current. Accordingly, the use of a specific resistive element over a particular contacting pad provides an intermediate level of resistance directly on the contacting pad of the test strip. When this intermediate level of resistance is connected to the meter through engagement with a corresponding meter connector contact, the meter can detect this "intermediate" level (e.g. through a circuit measurement of voltage drop by applying Ohm's and Kirchhoff's laws).

The detection of such an intermediate level can alert the meter's processor to access an entire new set of code data relating to test strip 10. In other words, providing a resistive element coating can be used to expand the number of codes available with a set number of contacting pads. For example, a strip may be formed with a particular code through a particular pattern of non-conducting insulating ink 75. When one of the conducting contacting pads is formed to include a particular resistive element, that same code represented by the pattern of non-conducting ink 75 now can be read by the meter to access an entirely different set of data. As an example, the contacting pad 66 of FIG. 6 (or any of the available contacting pads) could be formed to include a resistive element. As a non-limiting example, the resistive element could be provided in the form of a printed conductive ink. The thickness of the printed ink forming the resistive element, and resistivity of the ink composition, can be varied to achieve the desired resistance for a particular contacting pad. The additional information made available through this expansion of codes can include, but is not limited to, information related to hematocrit correction, information related to meter upgrades, information related to the particular strip type, or, as further discussed below, a checksum used in an error detection and rejection algorithm. Accordingly, the use of such a resistive element can be used to expand the number of code configurations available with a set number of contacting pads.

Consistent with an embodiment of the present invention, contacting pads 58, 60, 62, 64, and 66 may be used to represent individual unit values of a code, and when taken in combination, form a code value. In one embodiment, the contacting pads represent digital bits, which may be encoded in binary. That is, each of contacting pads 58, 60, 62, 64, and 66 may represent a binary value of "1" or "0" in the code, such that if contacting pad 58 is assigned a binary value of 1, it is equal to $2^{n-1}$, with n being the number of contacting pads. In the present example, contacting pad 58 would have a unit value of $2^4$ or 16, if there is a digital "1" assigned to it, or 0, if there is a digital "0" assigned to it. Similarly, contacting pad 60 may have a unit value of 8 or 0, contacting pad 62 may have a unit value of 4 or 0, contacting pad 64 may have a unit value of 2 or 0, and contacting pad 66 may have a unit value of 1 or 0. Thus, a code of 01010 has individual unit values of 0, 8, 0, 2, 0, and a combined code value of 10.

Consistent with embodiments of the present invention, contacting pads 58, 60, 62, and 64 may also have unit values other than the aforementioned digital bits. For example, contacting pads 58, 60, 62, and 64 may have unit values in the form of analog readings, symbols, or pictograms. Analog reading unit values may be related to actual readings of properties associated with contacting pads 58, 60, 62, and 64, such as the resistance, and the code value may be the combination of the individual resistances.

Symbol or pictogram unit values may be in the form of lines, shapes, pictures, etc. For example, contacting pad 58 may have a unit value of four lines, contacting pad 60 may have a unit value of three lines, and so on, such that the code value is equal to the total number of lines. In another example, contacting pads 58, 60, 62, 64, and 66 may have different shapes assigned to each pad, and the code value is the set of shapes. Symbols or pictograms may also be used in conjunction with digital bits and analog readings such that a digital "1" or "0", or an analog reading greater than or equal to a predetermined value enables the symbol or pictogram to be present on the contacting pad.

Contacting pads 58, 60, 62, 64, and 66 represent individual bits of the embedded code as discussed above, and as fully described in U.S. patent application Ser. No. 11/181,778, which is incorporated herein by reference in its entirety. As mentioned throughout this specification, consistent with an embodiment of the present invention, the embedded code may include information enabling an error detection or rejection method. In one embodiment consistent with the present invention, the error detection or rejection method uses a trending algorithm to detect and reject errors. For example, consider a vial containing fifty test strips. If the meter reads a code which is different than the last code read, and the number of the test strips used is less than fifty, the meter will indicate that there is a potential error. That is, consistent with an embodiment of the present invention, a trending algorithm uses recent and over-time trends as a basis for determining if a read code differs enough from an expected value to qualify as an error.

Figure 8:
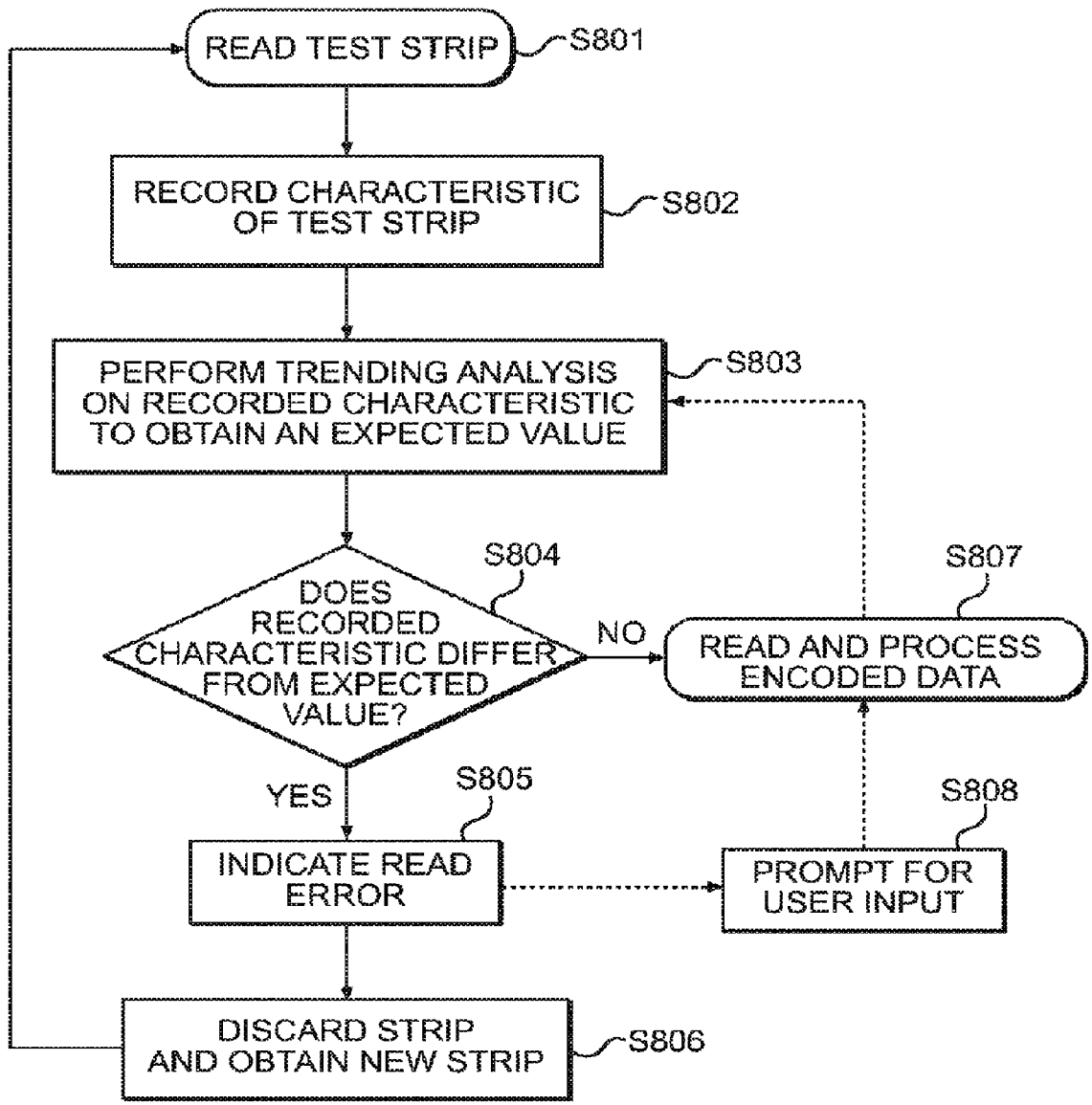
FIG. 8 is a flowchart illustrating a method for performing error detection and rejection using a trending algorithm, consistent with the present invention.

FIG. 8 is a flowchart illustrating a method for performing error detection and rejection using a trending algorithm, consistent with the present invention. First, test strip 10 is inserted into the meter, and read by the meter (S801). Next, a predetermined characteristic of the test strip is recorded, and saved in the memory of the meter (S802). The predetermined characteristic of the test strip may be any performance measure, including lot code or other manufacturing information regarding the test strip, or may be related to the property being measured by the test strip. A trending analysis is then performed on the recorded characteristic to obtain an expected value (S803). The trending analysis analyzes recorded characteristics from previously used test strips and the present test strip to obtain an expected value. The trending analysis may include performing averaging over the set of read test strips, or may include using a learning algorithm. Consistent with embodiments of the present invention, the learning algorithm may comprise an auto-adaptive learning algorithm, and may also include user feedback.

Returning to FIG. 8, the meter will then determine if the recorded characteristic of the present test strip differs from the calculated expected value (S804). If the recorded characteristic does not differ from the calculated expected value, the meter will read and process the encoded data (S807), and may store the encoded data as a data point to be included in the trending analysis. If the recorded characteristic differs from the calculated expected value, the meter will indicate a read error (S805), and the user may discard the test strip and obtain a new strip (S806). Alternatively, consistent with an embodiment of the present invention, if the recorded characteristic differs from the calculated expected value, the meter will indicate a read error (S805), and may prompt the user for additional input (S808). For example, referring to the earlier example of a vial containing fifty strips, after indicating a read error, the meter may ask the user whether the test strip is from a new vial, the lot code of the new vial, or may simply request that the user to re-enter the strip into the meter for re-reading. Depending on the answer to the prompt, the meter may then read and process the encoded data (S807), and then store the encoded data as a data point to be included in the trending analysis.

In another embodiment consistent with the present invention, the embedded code may include information enabling an error detection or rejection method which uses a checksum, which may include computing a modulus of the bits of the code, to detect and/or reject errors. In order to perform a checksum, additional checksum bits are embedded on test strip 10 along with the embedded code that is used to signal the meter to access any of the data referenced above particular to test strip 10. When test strip 10 is inserted into the meter, a code indicative of a checksum method is encoded thereon, and signals the meter to perform a checksum algorithm stored in a memory of the meter. In general, the meter executes an algorithm which determines the modulus of the calibration code, and compares it to an expected value. In a specific embodiment consistent with the present invention, the checksum method computes the modulus of the bits of the calibration code, and compares it to the modulus value also encoded on test strip 10. The read calibration code embedded on the test strip will be rejected if the computed modulus does not match the encoded modulus. The checksum bits may be encoded using a printed insulated pads, or by varying the resistance of the contact pads, as discussed above, or may be encoded by depositing an optical marker on contacting pads 58, 60, 62, 64, and 66. In an embodiment consistent with the present invention, the checksum bits may be encoded using a different method than the calibration bits. By encoding the checksum bits using a method that is different from the method used to encode the calibration bits, errors caused due to manufacturing tolerances will not be duplicated between the checksum and calibration bits, ensuring that the error will be rejected by virtue of a checksum which does not match. In embodiments consistent with the present invention, the checksum bits may be base 2 or binary, or may be based on other encoding methods. The checksum bits can also be encoded by known methods, such as using magnetic, or optical means (such as bar codes), notches cut into the substrate of test strip 10, and the like.

Consistent with an embodiment of the present invention, the checksum bits may be a parity bit, or single bit checksum, or may be a multiple bit checksum. A parity bit checksum allows for an error detection or rejection method which sacrifices only a single bit to detect an error. A parity bit checksum, however, will only protect against an odd number of bit read errors allowing an even number of bit read errors to go undetected. A parity bit checksum provides for 100% rejection of single bit errors and 50% detection and rejection for multi-bit errors. In an example consistent with a present invention, for a test strip having a binary system employing P number of contact pads for encoding information, as discussed above, will result in N codes where $N=2^P$. Utilizing a parity bit, the effective code space will be reduced to N/2 or $N=2^{P-1}$.

A multi-bit checksum is more robust than a parity bit checksum, but sacrifices more usable bits to accomplish the task. A multi-bit checksum provides a greater level of error detection and rejection, detecting both odd bit errors and some even bit errors. Using a multi-bit checksum, however, will use a greater number of bits and may not detect errors in bit order. Multi-bit checksums offer 100% rejection of single bit errors and at least 75% rejection of multi-bit errors depending on the number of bits for the checksum related to the calibration bits. For a binary system employing C number of checksum bits where C<P, the effective code space will be reduced to $N=2^{P-C}$.

Figure 9:
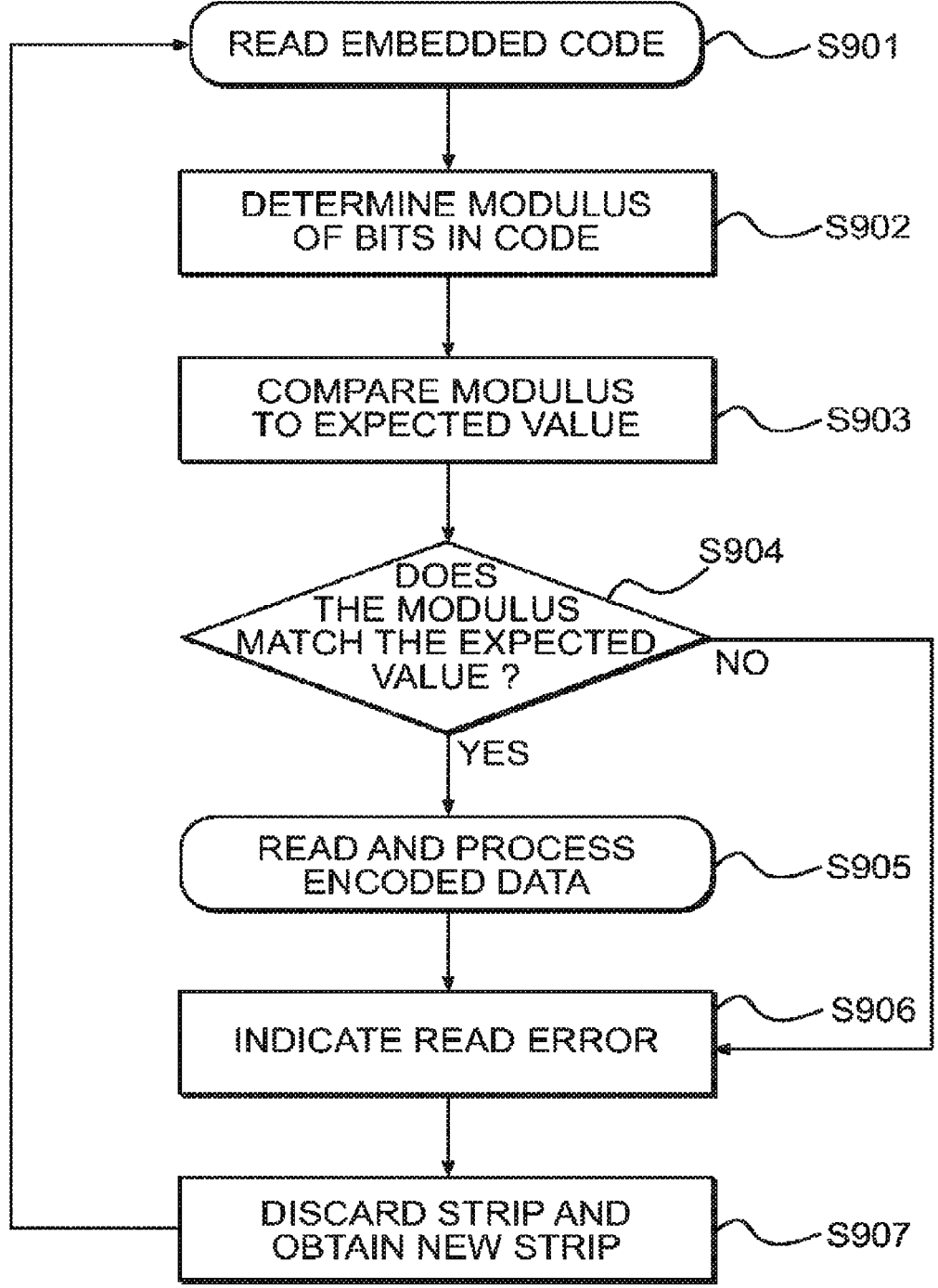
FIG. 9 is a flowchart illustrating a method for performing error detection and rejection using a checksum algorithm which computes the modulus of bits in a code, consistent with the present invention.

FIG. 9 is a flowchart illustrating a method for performing error detection and rejection using a checksum algorithm which includes computing a modulus of the bits in the code, consistent with the present invention, First, test strip 10 is inserted into the meter, and the code embedded thereon is read by the meter (S901). The meter includes a memory which contains instructions for instructing the meter's processor to determine the modulus of the code and compare it with a specific value. Within the code embedded on test strip 10 there is also an embedded expected value of the modulus, which the meter reads and stores in the memory. The meter then determines the modulus of the bits in the embedded code (S902), and compares the modulus to the stored expected value (S903). The meter determines if the expected value matches the modulus (S904). If the expected value and the modulus match, the meter will proceed to read and process the encoded data on test strip 10 indicative of any of the factors referenced above, including performing a test on a fluid sample, as specified by the information encoded on test strip 10 (S905). If the modulus of the bits does not match the expected value, the meter will indicate a read error (S906), and the user should discard the test strip and obtain a new one (S907).

In another embodiment consistent with the present invention, a redundant code may be encoded on test strip 10. Encoding test strip 10 with a redundant code enables the meter to detect and reject multiple bit read errors. A code, which may be indicative of the lot of the test strip, or any other factors as referenced above, is first encoded on test strip 10, and then the same, or redundant, code is again encoded on test strip 10, and both codes must match in order for the code to not be rejected by the meter. In an embodiment consistent with the present invention, the redundant iteration of the code is encoded in a different bit sequence than the original iteration of the code. When the original code and the redundant code are encoded in a different bit sequence, the codes are less susceptible to manufacturing location variation. By altering the bit sequence of the embedded codes variations due to physical shift or machine offset will not be translated into identical bit errors for both codes. This is advantageous, because, if the identical bit error is present in all embedded codes the error will go undetected.

In another embodiment consistent with the present invention, instead of encoding the redundant code in different bit sequence, the code may be encoded using different methods of manufacturing, or embedding the code, using a different method, such as, electrical, optical, or magnetic. Moreover, the use of a redundant code may further be combined with a checksum, as described above, for an increased level of error detection and rejection.

Figure 10:
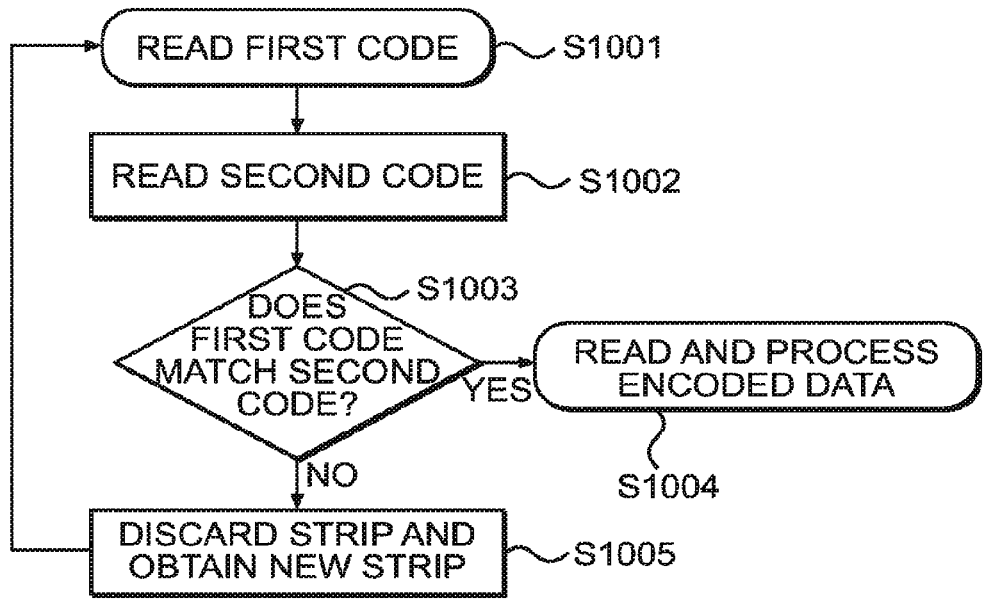
FIG. 10 is a flowchart illustrating a method for performing error detection and rejection using a redundant code, consistent with the present invention.

FIG. 10 is a flowchart illustrating a method for performing error detection and rejection using a redundant code, consistent with the present invention. First, test strip 10 is inserted into the meter, and the first code is read by the meter (S1001), and then the second code, which is a redundant iteration of the code, is read (S1002). The meter then determines if the first code matches the second code (S1003). If the first code and the second code match, the meter will proceed to read and process the encoded data on test strip 10 indicative of any of the factors referenced above, including performing a test on a fluid sample, as specified by the information encoded on test strip 10 (S1004). If the code and the second code do not match, a user discards test strip 10, and obtains a new strip, and starts the process again (S1005).

Consistent with another embodiment of the present invention a code reduction method may be utilized to provide error detection and rejection. Where the checksum and redundant coding methods disclosed above require exclusive bits which could otherwise be used for coding calibration lot information, the type of test, etc., a code reduction scheme utilizes all bits for coding information. In this embodiment, certain bit combinations, or codes, are identified as being excluded from a predetermined set of acceptable or valid codes. The set of valid codes may be stored in a memory of the meter. This method allows for the detection and rejection of multiple bit errors, and a possible level of error detection and rejection that may be greater than that of using a checksum or a redundant code.

Selectively reducing the amount of valid codes may be based on an exclusion set that can have a number of members M, where M>0 and M<N, where N is the number of possible codes. The set selected for exclusion is chosen to arrive at an acceptable level of error detection and rejection, while retaining an acceptable number of available codes. The set of codes selected for reduction, or the set of invalid codes, may be related to the number of 1s or 0s in a code, or may be related to the evenness or oddness of the bits. The means for exclusion are not limited to these example, but may be found to be easier to implement.

As an example, for a binary system employing P number of pads for encoding an error detection and rejection code will result in N codes where $N=2^P$. By selectively reducing the number of valid codes by, for example, eliminating values where the code has a count of 1s which is equal to Y, where Y≤P, the count of 1s (or 0s) are symmetric where the count of zero 1s equals the count of P 1s and the count of two 1s equals the count of P−1 1s.

As another example, using a binary system where P=5 results in a code space of N=32, and has a zero percent detection/rejection rate, i.e., all codes are valid. By selectively excluding codes that have a value containing two 1s, the possible number of codes is reduced by 10 to 22 and results in a possible detection/rejection rate of 45.5%. Similarly, a lower level of protection can be selected by selectively excluding codes that have a value containing one or zero 1s. Because there are five possible codes which have one 1, and one possible code that has zero 1s, the code space is reduced by six to 26 possible codes, and results in an error detection/rejection rate of 23%. That is, the percentage of invalid codes, resulting from manufacturing defects, etc., that will be detected and rejected by the meter, is 23%.

Consistent with the present invention, the above described methods of selectively excluding codes is extended to the possible code values and unit values, as discussed above. For example, consider a four unit code comprised of unit values in the set of {A, B, C, D}. The possible code values from this set would include {A, B, C, D}, {B, B, C, D}, {C, B, C, D}, {D, B, C, D}, {A, C, C, D}, and so on including all possible sequences and iterations of {A, B, C, D}. Due to known tolerances, certain code values, or certain unit values may have a higher propensity of having errors associated therewith. For example, the code value {D, D, A, C}, or the unit value of a fourth position {A}, may be known to have a high error rate, or a high probability of being misread as a different code value or unit value. Accordingly, a set of code values or unit values which are likely to be erroneous could be generated as an exclusion set, or conversely a set of acceptable code values, such that unit values or code values having a high error rate, or which generate serious errors, can be excluded. This method can be further applied to unit values such as digital bits, analog readings, symbols, or pictograms, as described above.

Figure 11:
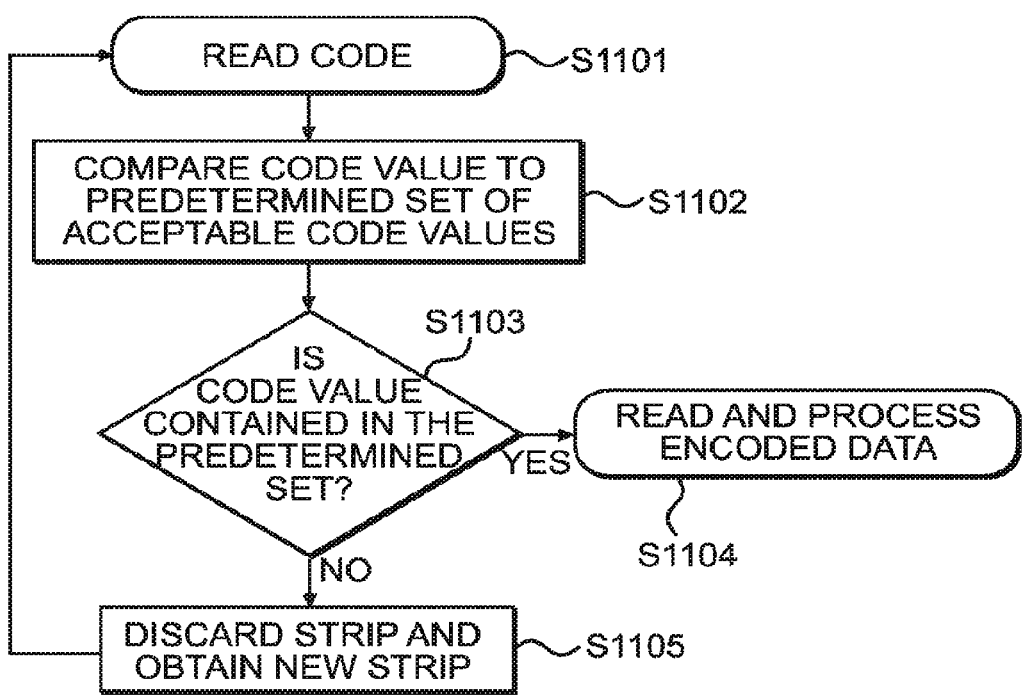
FIG. 11 is a flowchart illustrating a method for performing error detection and rejection using a method of selectively reducing the number of available codes, consistent with the present invention.

FIG. 11 is a flowchart illustrating a method for performing error detection and rejection using a method of selectively reducing the number of available code values, consistent with the present invention. This method may also be applied by selectively reducing certain unit values, as well. First, test strip 10 is inserted into the meter, and the code embedded thereon is read by the meter (S1101). The meter compares the code value with a predetermined set of acceptable code values, which may be stored in the memory of the meter (S1102). The meter determines if the code value on test strip 10 matches a code value that is on the predetermined set of acceptable code values (S1103). The predetermined set of acceptable code values, in one embodiment consistent with the present invention, contains code values which have the highest probability of not containing an error based on known manufacturing tolerances and conditions. If the code value on test strip 10 matches a code value on the predetermined set of acceptable code values, the code value is determined to be a valid code, and the meter will proceed to read and process the encoded data on test strip 10 indicative of any of the factors referenced above, including performing a test on a fluid sample, as specified by the information encoded on test strip 10 (S1104). If the code value does not match a code value contained on the predetermined set of acceptable code values, test strip 10 likely contains manufacturing defects, the meter will indicate an error and the user should discard the strip and obtain a new strip (S1105).

TABLE 1

| | Errors | | | | Error codes | | | |
|---|---|---|---|---|---|---|---|---|
| Code | Bit 3 | Bit 2 | Bit 1 | Bit 0 | Bit 3 | Bit 2 | Bit 1 | Bit 0 |
| 0000 | 1000 | 0100 | 0010 | 0001 | 8 | 4 | 2 | 1 |
| 0001 | 1001 | 0101 | 0011 | 0000 | 9 | 5 | 3 | 0 |
| 0010 | 1010 | 0110 | 0000 | 0011 | 10 | 6 | 0 | 3 |
| 0011 | 1011 | 0111 | 0001 | 0010 | 11 | 7 | 1 | 2 |
| 0100 | 1100 | 0000 | 0110 | 0101 | 12 | 0 | 6 | 5 |
| 0101 | 1101 | 0001 | 0111 | 0100 | 13 | 1 | 7 | 4 |
| 0110 | 1110 | 0010 | 0100 | 0111 | 14 | 2 | 4 | 7 |
| 0111 | 1111 | 0011 | 0101 | 0110 | 15 | 3 | 5 | 6 |
| 1000 | 0000 | 1100 | 1010 | 1001 | 0 | 12 | 10 | 9 |
| 1001 | 0001 | 1101 | 1011 | 1000 | 1 | 13 | 11 | 8 |
| 1010 | 0010 | 1110 | 1000 | 1011 | 2 | 14 | 8 | 11 |
| 1011 | 0011 | 1111 | 1001 | 1010 | 3 | 15 | 9 | 10 |
| 1100 | 0100 | 1000 | 1110 | 1101 | 4 | 8 | 14 | 13 |
| 1101 | 0101 | 1001 | 1111 | 1100 | 5 | 9 | 15 | 12 |
| 1110 | 0110 | 1010 | 1100 | 1111 | 6 | 10 | 12 | 15 |
| 1111 | 0111 | 1011 | 1101 | 1110 | 7 | 11 | 13 | 14 |

In another embodiment consistent with the present invention, an arrangement method is used to minimize the impacts of possible bit errors. In situations where the utilization of a bit error detection and rejection scheme is less than optimal, limiting the impact of a bit error is an acceptable alternative. Bits embedded on test strip 10 typically have different probabilities of being prone to an error. These differing probabilities can be used to minimize the impact of a possible bit error by constructing a logical arrangement placing the bits at different locations than their actual physical locations to reduce the impact of a bit error. Table 1, below, shows a 16 codes in a 4-bit binary coding scheme, and the possible single bit errors. The erroneous codes are determined by summing the bits wherein a 1 in the $3^{rd}$ bit equals 8, a 1 in the $2^{nd}$ bit equals 4, a 1 in the $1^{st}$ bit equals 2, and a 1 in the $0^{th}$ bit equals 1.

Figure 12:
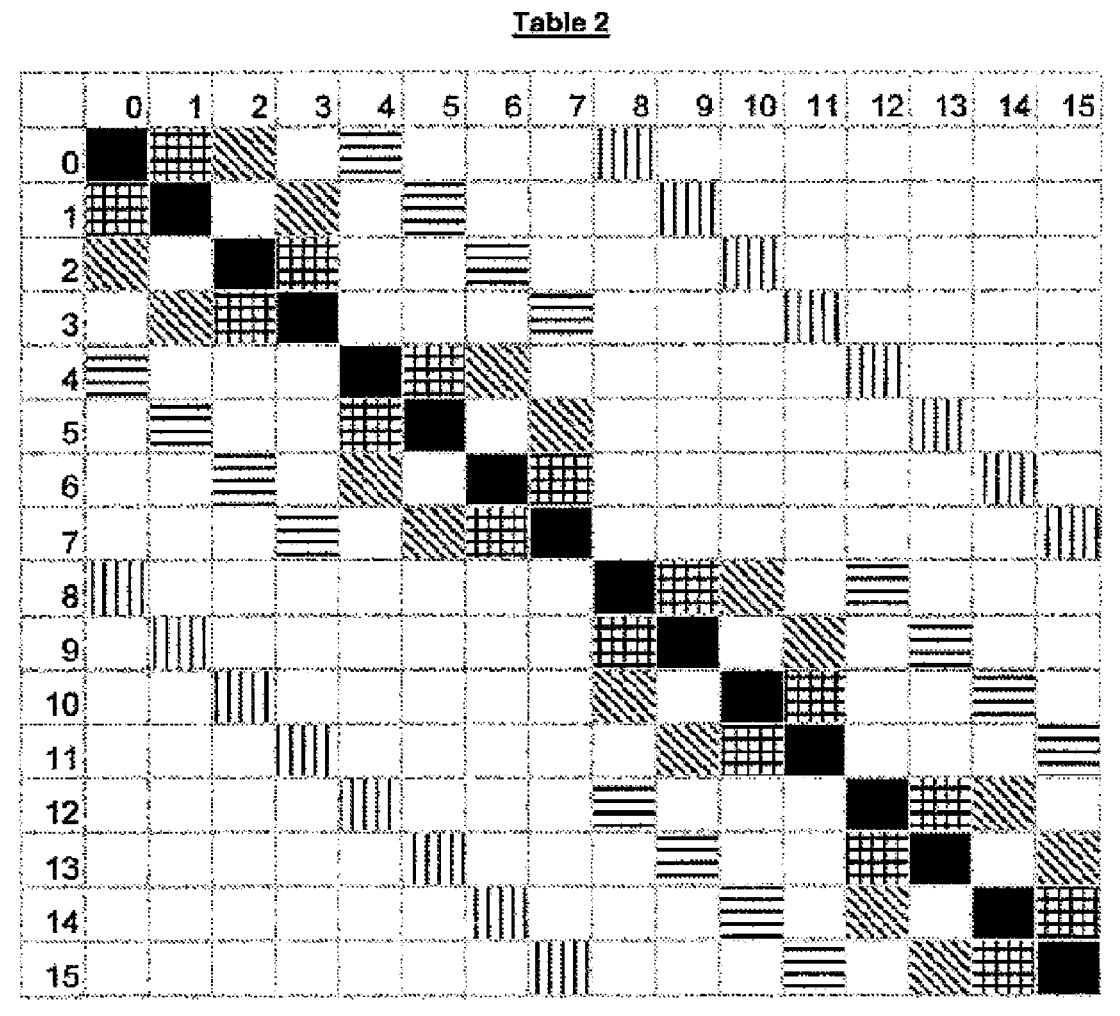

As shown in Table 1 all possible binary codes have four possible single bit errors. The results of Table 1 are further shown in Table 2, illustrated in FIG. 12. Table 2 shows the same results using an error grid. Table 2 shows just how close or far away from the expected code, a single bit error will cause the read code to deviate. The vertical numbers correspond to the intended (actual) code number, and the horizontal numbers correspond to the actually read code numbers. Solid black shading indicates the expected code, grid lines indicate the least significant bit error, diagonal lines indicate the next significant bit error, horizontal lines indicate the next significant bit error, and vertical lines indicate the most significant bit error.

Due to manufacturing tolerances, and the likelihood of particular bits being incorrect and causing an error, certain codes have higher probabilities of having particular single bit errors, and certain single bit errors will cause a read code to deviate more from the expected than others, as is illustrated in Table 2. By constructing a logical arrangement of the codes with respect to the most significant bit error and the least significant bit error, it can be minimized as to how far a code can stray from the expected, and still produce an acceptable result. From this logical arrangement, the codes having a predetermined probability of acceptable bit errors may be used as a code space and accepted, regardless of an error in the least significant bit, as they will have a lesser effect on the magnitude of the measured property.

Figure 13:
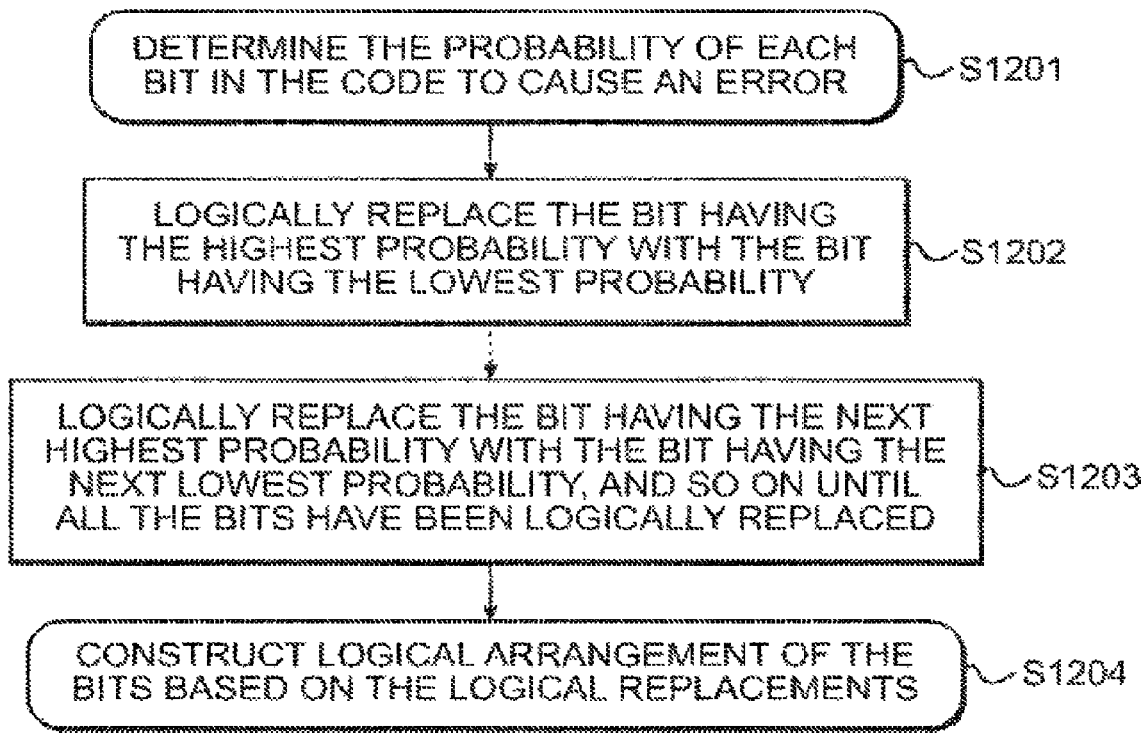
FIG. 13 is a flowchart for illustrating a method for constructing a logical arrangement consistent with an embodiment of the present invention.

FIG. 13 is a flowchart for illustrating a method for constructing a logical arrangement consistent with an embodiment of the present invention. First, the probability of each bit in the code to be erroneous is determined (S1201), The probability may be due to, for example, manufacturing tolerances. As an example, referring to test strip 10 having contacting pads 58, 60, 62, 64, and 66, the bit encoded by pad 58 is likely to have the highest probability of having an error because it is at an edge of the strip, wherein manufacturing processes are more likely to damage or misproduce contacting pad 58. Conversely, an interior pad, such as contacting pad 62, has the lowest probability of having an error. Accordingly, the bit having the highest probability of having an error is logically replaced by the bit having the lowest probability of having an error (S1202). Next, in a similar process, the bit having the next highest probability of having an error is logically replaced by the bit having the next lowest probability of having an error, and so on, until all bits have been logically replaced (S1203). After all of the bits have been logically replaced, a logical arrangement of the bits is constructed (S1204). The logical arrangement would result in the bits being laid out in a sequence which is different than the sequence in which they appear on test strip 10. For example a logical arrangement of test strip 10 with contacting pads in the sequence of 58, 60, 62, 64, and 66, may appear as 62, 66, 58, 64, 60.

Moreover, the logical arrangement may be performed in two ways, a sequential arrangement, wherein the logical bits are arranged to keep the code in sequence, or a non-sequential arrangement, wherein the original bits remain in sequence, but the resulting code space is arranged logically, based on the logical replacements. The logical arrangement determines how the meter reads the actual code that is embedded on the test strip. That is, in a sequential arrangement, the meter will read the test strip as having the logical code arrangement, and in a non-sequential arrangement, the meter will read the test strip as having the actual code, but correlate the actual code to the logical code space which is created from the logical arrangement. Moreover, the result of using the sequential or non-sequential arrangement methods is creating a code space to be recognized by the meter as having acceptable codes, such that a test strip having a code with the least significant bit errors will be acceptable, and having a code with the most significant bit errors will not be acceptable.

Further consistent with an embodiment of the present invention, a method for performing an error correction may be used to correct codes that have been rejected, or detected as having bit code errors. For example, consistent with the present invention, a Hamming code can effectively be used to correct errors since the number of bits encoded on the test strips has a fixed length. Hamming codes are well known in telecommunications, and are used to protect against errors in transmitted digital data, or scanned data, such as magnetic stripe or bar code. A Hamming code typically uses additional error correction or error check bits which are encoded along with the encoded information, such that the additional error correction/check bits are arranged such that different incorrect bits produce different error results, allowing for the identification and correction of the bit error. Specifically, a Hamming code includes three error check bits for every four bits of encoded information, and can correct any single-bit error, and detect all single-bit and two-bit errors.

To include a Hamming code on test strip 10 consistent with the present invention, three error check bits would have to be added onto test strip 10 for every four bits of information. The error check bits may be encoded onto test strip 10 using a printed insulated pads, or by varying the resistance of the contact pads, as discussed above, or may be encoded by depositing an optical marker on contacting pads 58, 60, 62, 64, and 66. As an example, using test strip having contacting pads 58, 60, 62, 64, and 66 as described above, with one contacting pad being used to designate an auto-wake feature, test strip contains four usable pads, and four bits. By varying the resistance or depositing an optical marker on contacting pads 58, 60, 62, 64, and 66, three extra error check bits can be encoded on to use a Hamming code.

Moreover, the above methods are not necessarily exclusive, and can be used in combination to provide a greater level of error detection and rejection than a single method alone. For example, the use of a checksum can be combined with the reduced code set. Moreover, a modulus or checksum may be used in combination with a Hamming code, enabling the detection of a bit error at a higher level than either method alone, and the subsequent correction of the bit error.

Although a Hamming code is well known and has been used to correct dynamically transmitted codes, a Hamming code has not been used to correct a statically read code, such as the code consistent with the present invention. Moreover, because the bits encoded on the test strips of the present invention are statically read and cannot be retransmitted upon error detection, error correction such as by using a Hamming code may be beneficial in saving the user time and money, by not having to discard test strip 10 on the detection of an error, Combining the methods discussed above, e.g., such as a modulus with a reduced code set is also possible.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A system for measuring a property of a sample fluid, comprising:
    a diagnostic measuring device having a connector configured to receive a test strip for collecting the sample fluid, the strip having information including a first code embedded thereon, the first code comprising a plurality of bits arranged in a physical arrangement; and
    the diagnostic device further comprising a controller programmed to perform an error detection routine comprising:
    reading the plurality of bits of the first code;
    determining a probability of each bit to cause a read error in the first code;
    constructing a logical arrangement of the bits different than the physical arrangement based on the probability, wherein the logical arrangement results in a logically arranged code comprising the bits arranged such that the impact of potential read errors is minimized;
    performing an error detection and rejection algorithm on the logically arranged code; and
    determining the constituent level of the sample fluid if the error detection and rejection algorithm detects an acceptable error or does not detect an error in the logically arranged code.

2. The system according to claim 1, wherein the logical arrangement comprises the bits arranged such that the hit having the highest probability of causing a read error is logically replaced by the bit having the lowest probability of causing a read error, and the bit having the lowest probability of causing a read error is logically replaced by the bit having the highest probability of causing a read error.

3. The system according to claim 2, wherein the logical arrangement results in the logically arranged code which is read in sequence.

4. The system according to claim 2, wherein the logical arrangement results in the logically arranged code which is not read in sequence.

\* \* \* \* \*

UNITED STATES PATENT AND TRADEMARK OFFICE
CERTIFICATE OF CORRECTION

PATENT NO. : 10,013,297 B2
APPLICATION NO. : 14/683484
DATED : July 3, 2018
INVENTOR(S) : Brent E. Modzelewski et al.

Page 1 of 1

It is certified that error appears in the above-identified patent and that said Letters Patent is hereby corrected as shown below:

In the Claims

In Claim 2, Column 18, Line 59:
Delete "hit"
Insert --bit--

Signed and Sealed this
Second Day of October, 2018

Andrei Iancu
*Director of the United States Patent and Trademark Office*